United States Patent
Lennartz et al.

(10) Patent No.: US 11,701,095 B2
(45) Date of Patent: Jul. 18, 2023

(54) ROBOTIC SURGICAL SYSTEMS AND METHODS OF USE THEREOF

(71) Applicant: Covidien LP, Mansfield, MA (US)

(72) Inventors: Amanda H. Lennartz, Erie, CO (US); Kenlyn Bonn, Lakewood, CO (US); Tyler J. Bagrosky, Arvada, CO (US); Michael B. Lyons, Boulder, CO (US)

(73) Assignee: Covidien LP, Mansfield, MA (US)

( * ) Notice: Subject to any disclaimer, the term of this patent is extended or adjusted under 35 U.S.C. 154(b) by 291 days.

(21) Appl. No.: 16/953,476

(22) Filed: Nov. 20, 2020

(65) Prior Publication Data

US 2021/0153855 A1     May 27, 2021

Related U.S. Application Data

(60) Provisional application No. 62/938,555, filed on Nov. 21, 2019.

(51) Int. Cl.
| | |
|---|---|
| *A61B 17/00* | (2006.01) |
| *A61B 17/3205* | (2006.01) |
| *A61F 5/00* | (2006.01) |
| *A61B 34/30* | (2016.01) |

(52) U.S. Cl.
CPC .... *A61B 17/00491* (2013.01); *A61B 17/3205* (2013.01); *A61F 5/0083* (2013.01); *A61B 34/30* (2016.02); *A61B 2017/005* (2013.01); *A61B 2017/00818* (2013.01)

(58) Field of Classification Search
CPC .......... A61B 17/00491; A61B 17/3205; A61B 34/30; A61B 34/35; A61B 34/37; A61B 2017/005; A61B 2017/00818; A61B 2017/308; A61B 2018/00494; A61B 2018/00601; A61B 2034/107; A61B 2034/2055; A61B 2034/302; A61B 90/39; A61B 2090/3908; A61B 2090/3912; A61B 2090/3945; A61B 2090/395; A61B 18/00; A61F 5/0083
See application file for complete search history.

(56) References Cited

U.S. PATENT DOCUMENTS

| | | | |
|---|---|---|---|
| 8,753,333 B2 | 6/2014 | Johnson et al. | |
| 9,123,155 B2 | 9/2015 | Cunningham et al. | |
| 9,592,095 B2 | 3/2017 | Panescu et al. | |
| 10,188,451 B2 | 1/2019 | Peterson et al. | |
| 10,607,345 B2 | 3/2020 | Carnes et al. | |
| 2003/0065069 A1* | 4/2003 | Wojciak | C08K 5/0041 524/205 |
| 2006/0020167 A1* | 1/2006 | Sitzmann | A61B 1/00181 606/1 |
| 2008/0114334 A1* | 5/2008 | Voegele | A61B 90/39 606/167 |
| 2009/0012544 A1* | 1/2009 | Thompson | A61B 17/1114 606/156 |

(Continued)

*Primary Examiner* — Jocelin C Tanner
(74) *Attorney, Agent, or Firm* — Carter, Deluca & Farrell LLP

(57) ABSTRACT

A method of performing bariatric surgery using a robotic surgical system includes positioning a gastrectomy device in a selected location in a stomach; applying an adherent material to the stomach along a desired transection line; and cutting the stomach along the desired transection line delineated by the adherent material.

15 Claims, 4 Drawing Sheets

(56) References Cited

U.S. PATENT DOCUMENTS

| | | | |
|---|---|---|---|
| 2009/0248022 A1* | 10/2009 | Falkenstein | A61B 18/16 |
| | | | 606/51 |
| 2010/0081864 A1* | 4/2010 | Hess | A61B 17/3423 |
| | | | 600/101 |
| 2010/0081883 A1* | 4/2010 | Murray | A61B 17/00234 |
| | | | 600/204 |
| 2012/0255986 A1* | 10/2012 | Petty | A61F 5/0086 |
| | | | 227/176.1 |
| 2014/0114121 A1* | 4/2014 | Trivedi | A61F 5/0083 |
| | | | 600/37 |
| 2015/0133740 A1* | 5/2015 | Dierking | A61B 90/30 |
| | | | 600/249 |
| 2015/0223868 A1 | 8/2015 | Brandt et al. | |
| 2016/0015544 A1* | 1/2016 | Holsten | A61F 5/0089 |
| | | | 600/37 |
| 2020/0188044 A1* | 6/2020 | Penny | A61B 34/37 |
| 2020/0222111 A1 | 7/2020 | Yates et al. | |

\* cited by examiner

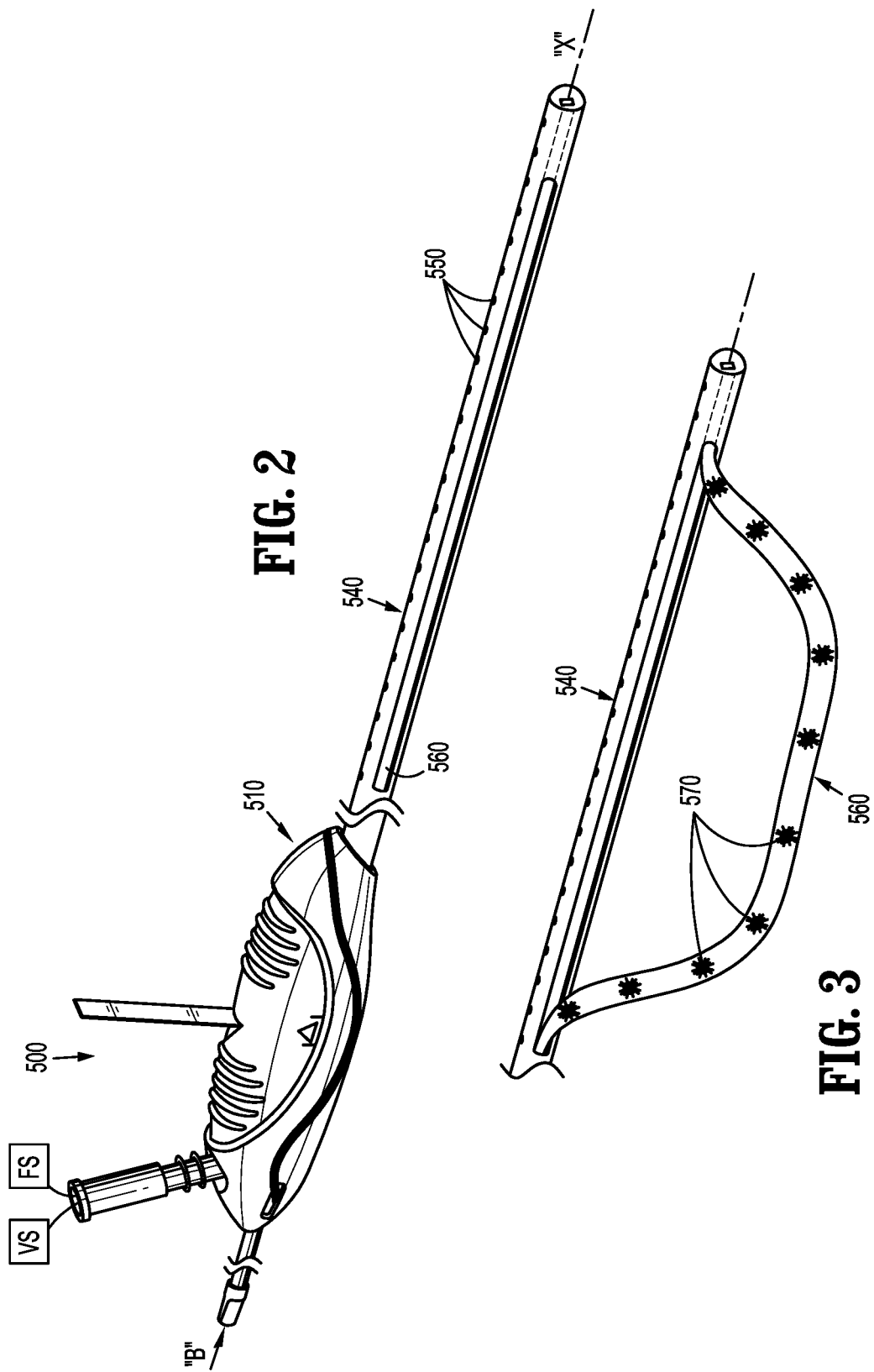

ROBOTIC SURGICAL SYSTEMS AND METHODS OF USE THEREOF

CROSS-REFERENCE TO RELATED APPLICATION

This application claims the benefit of and priority to U.S. Provisional Application No. 62/938,555, filed on Nov. 21, 2019, the entire contents of which being incorporated by reference herein.

INTRODUCTION

This disclosure is generally related to the field of robotic surgery, and more particularly to robotic surgical systems used in performing bariatric surgical procedures.

BACKGROUND

Various bariatric procedures such as gastric bypass, adjustable gastric banding, and sleeve gastrectomy, have been developed for treating people who have obesity. Sleeve gastrectomy involves transecting a stomach using a suitable device to reduce a stomach volume. Sleeve gastrectomy procedures are often aided by the use of a gastric tube, which serves as a guide or template for transecting the stomach to the appropriate configuration while inhibiting inadvertent transection of stomach or esophageal tissue. Once the stomach has been appropriately transected, the gastric tube is removed and a leak test is performed to determine whether there are any areas of extravasation.

During a bariatric procedure, a clinician may find it challenging to trasect the stomach along a straight line when using certain surgical instruments. This may be due to the overall lack of maneuverability of the surgical instrument or the challenge in maintaining a steady hand while simultaneously performing an activation of the surgical instrument. Accordingly, it may be beneficial to have a robot perform the stomach transection along the desired transection line.

SUMMARY

In one aspect, the present disclosure provides a method of performing bariatric surgery using a robotic surgical system including positioning a gastrectomy device in a selected location in a stomach; manually applying an adherent material to the stomach along a desired transection line; and cutting the stomach along the desired transection line delineated by the adherent material using a robotically-controlled surgical instrument.

In aspects, the method may further include activating the adherent material to render the adherent material visible to the robotic surgical system.

In aspects, activating the adherent material may include applying heat to the adherent material.

In aspects, activating the adherent material may include applying energy to the adherent material.

In aspects, applying energy to the adherent material may include emitting light from the gastrectomy device.

In aspects, the adherent material may be a surgical glue.

In aspects, the method may further include moving a sail member of the gastrectomy device from an unexpanded configuration to an expanded configuration prior to applying the adherent material to the stomach.

In another aspect, the present disclosure provides a method of performing bariatric surgery using a robotic surgical system including positioning a gastrectomy device in a selected location in a stomach; expanding a sail member of the gastrectomy device relative to an elongated member of the gastrectomy device to engage a greater curvature of the stomach and urge the elongated member into complementary mating relation with a lesser curvature of the stomach; moving a marking device along the stomach to define a desired transection line along the stomach; and transecting the stomach along the desired transection line using a robotically-controlled surgical instrument.

In aspects, moving the marking device may include applying a physical marking on the stomach.

In aspects, the physical marking may be formed by at least one of a material applied to the stomach or heat applied to the stomach.

In aspects, the material may be a surgical glue, and the method further comprises applying heat to the surgical glue, thereby sealing the transection line.

In aspects, the robotically-controlled surgical instrument may be an electrosurgical instrument that cuts the stomach along the transection line and applies heat to the stomach along the transection line.

In aspects, the robotically-controlled surgical instrument automatically transects the stomach along the desired transection line by following the physical marking on the stomach.

In aspects, the marking device may be manually moved by a clinician to define the desired transection line along the stomach.

In another aspect, the present disclosure provides a method of performing a surgical procedure using a robotic surgical system including manually moving a marking device along tissue while applying a surgical glue to the tissue with the marking device, thereby defining a transection line along the tissue; applying energy to the surgical glue, thereby enhancing a visibility of the surgical glue to the robotic surgical system; and cutting the tissue along the transection line using a robotically-controlled surgical instrument.

In aspects, the robotically-controlled surgical instrument follows behind the marking device and cuts the tissue along the transection line as the marking device moves along the tissue.

In aspects, the method may further include applying heat to the tissue along the transection line using the robotically-controlled surgical instrument concurrently with cutting the tissue.

In aspects, the heat applied to the tissue by the robotically-controlled surgical instrument cures the surgical glue to effect a seal of the tissue along the transection line.

In aspects, the method may further include positioning a gastrectomy device in a selected location in a stomach prior to moving the marking device; expanding a sail member of the gastrectomy device relative to an elongated member of the gastrectomy device to engage a greater curvature of the stomach and urge the elongated member into complementary mating relation with a lesser curvature of the stomach.

In aspects, the method may further include emitting light from a plurality of lights disposed along the sail member, wherein the surgical glue is applied to the stomach along a pathway defined by the plurality of lights.

BRIEF DESCRIPTION OF DRAWINGS

FIG. 2 is a perspective view illustrating a gastrectomy device of the robotic surgical system of FIG. 1 with a sail member of the gastrectomy device shown in an unexpanded state;

FIG. 3 is an enlarged perspective view illustrating a distal end portion of the gastrectomy device of FIG. 2 with the sail member in an expanded state;

Figure 1:
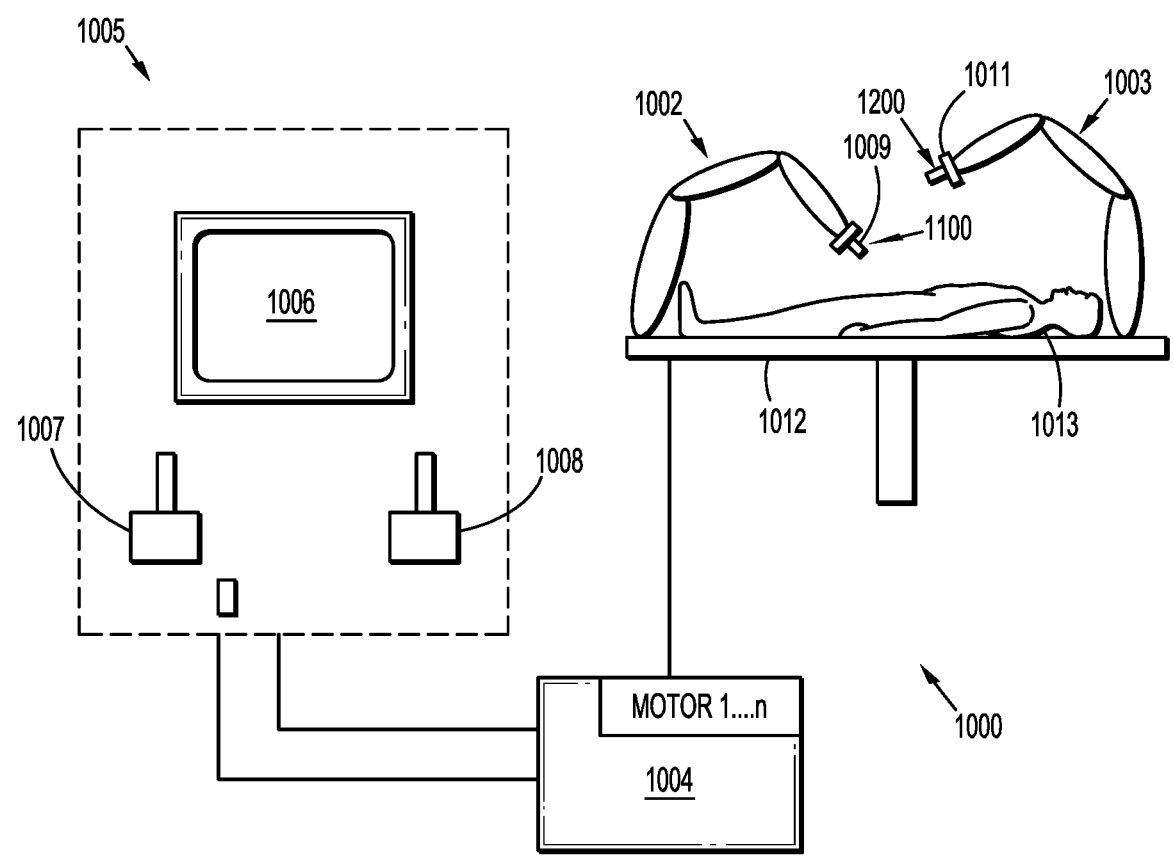
FIG. 1 is a schematic diagram of a robotic surgical system provided in accordance with aspects of the present disclosure.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Embodiments of the presently disclosed robotic surgical system are described in detail with reference to the drawings, in which like reference numerals designate identical or corresponding elements in each of the several views. As used herein, the term "distal" refers to that portion of the robotic surgical system, or component thereof, farther from the user, while the term "proximal" refers to that portion of the robotic surgical system, or component thereof, closer to the user.

As used herein, the terms parallel and perpendicular are understood to include relative configurations that are substantially parallel and substantially perpendicular up to about + or −10 degrees from true parallel and true perpendicular. In the following description, well-known functions or construction are not described in detail to avoid obscuring the disclosure in unnecessary detail.

The present disclosure is generally directed to a robotic surgical system configured to perform a robotic-assisted sleeve gastrectomy procedure. In aspects of the disclosure, a clinician manually marks the stomach to define a desired transection line and the robotic surgical system transects the stomach along the line marked by the clinician. The transection line may be physically marked on the stomach by the clinician utilizing an electrosurgical instrument to cauterize the stomach tissue or by applying an adherent material, such as a surgical glue, to the stomach tissue. In aspects, the desired transection line may be generated by the robotic surgical system, whereby the clinician confirms the placement and the accuracy of the desired transection line. The robotic surgical system may include a suitable sensor configured to locate the transection line marked by the clinician to enable transection of the stomach tissue along the marked transection line. In aspects of the disclosure, a surgical glue used to mark a transection line is activated by heat generated by use of an electrosurgical transecting instrument to transect the stomach tissue along the transection line, thereby sealing the tissue along the transection line.

In some aspects, a gastrectomy device may be provided that defines a transection line on a stomach using an array of lights. A robotically-controlled surgical instrument may be equipped with a suitable sensor configured to locate the transection line marked by the lights to enable transection of the stomach tissue along the transection line. In some aspects, a non-conductive bowel cutting guide may be provided that protects the bowel while allowing for fast cutting.

With reference to FIG. 1, a robotic surgical system exemplifying the aspects and features of the present disclosure is shown identified by reference numeral 1000. Robotic surgical system 1000 includes a plurality of robot arms 1002, 1003; a control unit 1004; and an operating console 1005 coupled with control unit 1004. Operating console 1005 may include a display device 1006, which may be set up in particular to display three-dimensional images, and manual input devices 1007, 1008 that enable a surgeon to telemanipulate robot arms 1002, 1003 in a first operating mode. Robotic surgical system 1000 may be configured for use on a patient 1013 lying on a patient table 1012 to be treated in a minimally invasive manner.

Each of the robot arms 1002, 1003 may include a plurality of segments, which are connected through joints, and an attaching device 1009, 1011, to which may be attached, for example, an end effector assembly 1100, 1200, respectively, such as, for example, a gastrectomy device or an electrosurgical instrument (e.g., a vessel sealer, a transection device, a cautery device). Robot arms 1002, 1003 and end effector assemblies 1100, 1200 may be driven by electric drives, e.g., motors, that are connected to control unit 1004. Control unit 1004 (e.g., a computer) may be configured to activate the motors or deliver electrosurgical energy, in particular by means of a computer program, in such a way that robot arms 1002, 1003, their attaching devices 1009, 1011, and end effector assemblies 1100, 1200 execute a desired movement and/or function according to a corresponding input from manual input devices 1007, 1008, respectively. Control unit 1004 may also be configured in such a way that it regulates the movement of robot arms 1002, 1003 and/or of the motors.

The end effector assembly 1100 or 1200 may be any surgical instrument suitable for use with the robotic surgical system 1000 including, but not limited to, a bipolar instrument, a monopolar instrument, an ablation instrument, a thermal treatment instrument, an ultrasonic instrument, a microwave instrument, or a radiofrequency instrument. In aspects of the disclosure, the end effector assembly 1100 or 1200 may be an electrosurgical instrument having opposing jaw members (not shown) that mutually cooperate to grasp, seal, and divide tissue. In some aspects, the end effector assembly 1100 or 1200 may be a surgical stapling device, a suturing device, or the like.

Referring now to FIGS. 2 and 3, a gastrectomy device 500 is provided and configured to be manually operated by a clinician for use in a surgical procedure, such as, for example, a sleeve gastrectomy procedure. In other aspects, the gastrectomy device 500 may be configured to be connected to the robot arm 1003 and robotically-controlled by the robotic surgical system 1000. The gastrectomy device 500 generally includes a handle assembly 510, an elongated shaft member 540 extending distally from the handle assembly 510, and a sail member 560 (e.g., a tube) associated with the elongated shaft member 540. The handle assembly 510 of the gastrectomy device 500 is further configured for connection to a pressure source (e.g., an insufflation source "FS") or a negative pressure source (e.g., a vacuum source "VS").

The sail member 560 is integrally formed with or otherwise fixedly mated to the elongated shaft member 540 such that distal movement of the sail member 560 causes the sail member 560 to expand or bow outwardly relative to the elongated shaft member 540. More specifically, distal movement of the sail member 560 causes the sail member 560 to move from a first state, as shown in FIG. 2, in which the sail member 560 is parallel with a longitudinal axis "X" defined by the elongated shaft member 540, to a second state, as shown in FIG. 3, in which the sail member 560 bows out from the longitudinal axis "X" to form an arc. In the second state, the sail member 560 defines a configuration that generally complements the curvature of a greater curvature portion of a stomach "S" (FIG. 4).

The gastrectomy device 500 includes an array of lights 570 associated with the sail member 560. The lights 570 provide a visual reference of the position of the sail member 560 and/or gastrectomy device 500 generally. In some embodiments, the array of lights 570 may be integrally formed with the sail member 560. The gastrectomy device 500 includes a power source (not shown) in the form of a battery or any suitable power source for supplying power to the array of lights 570. In some embodiments, the array of lights 570 may include an integral power source or may be wirelessly coupled (e.g., inductively) to a source of power that is external to the patient.

The robotic arm 1002 of the robotic surgical system 1000 may have a light sensor or an infrared sensor configured to detect the light and/or heat emitted by the array of lights 570 to allow the robotic arm 1002 to follow the path created by the lights 570. The surgical instrument attached to the robotic arm 1002 may be configured to transect the stomach along the path delineated by the array of lights 570.

Figure 4:
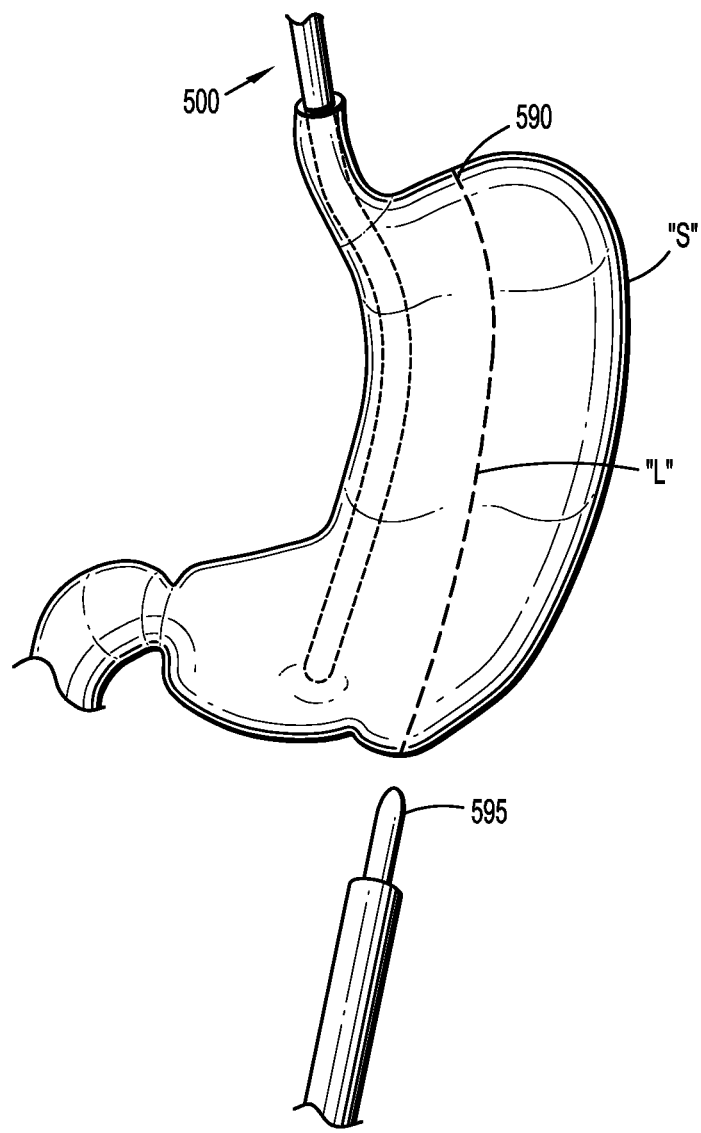
FIG. 4 is a perspective view illustrating the gastrectomy device and a marking device of the robotic surgical system of FIG. 1 in use.

With reference to FIG. 4, the robotic surgical system 1000 may include a marking device 595 configured to disperse an adherent material 590 to mark a desired transection line on the stomach "S". The adherent material 590 may be a any suitable surgical glue and/or filler (e.g., fibrin sealant, cyanoacrylate, polyethylene glycol polymer, gelatin, thrombin, or any other suitable glue or filler). The adherent material 590 may be configured to undergo a change in color or illuminate upon activation by an external stimuli to be rendered more visible to a camera (not explicitly shown) of the robotic surgical system 1000. For example, heat emitted by the lights 570 of the gastrectomy device 500 may illuminate the adherent material 590, thus printing a visible line along the desired transection line. It is contemplated that any suitable surgical instrument may utilized to apply energy (e.g., infrared, microwave, etc.) to the adherent material 590 to activate the adherent material 590. An activation of the adherent material 590 may also include a curing of the adherent material 590 to assist in sealing tissue after transecting the selected portion of the tissue. In other aspects, the adherent material 590 may be visible to the robotic surgical system 1000 (e.g., a camera) without having to first be activated.

In other aspects, the marking device 595 may be a vessel sealer or other surgical instrument configured to cauterize tissue, such that the marking device 595 may physically mark the tissue along the desired transection line. The robot arm 1002 may be configured to identify the cauterized marking of the tissue and move the attached vessel sealer along the path created by the marking. For example, the robotic surgical system 1000 may have an imaging device that identifies the color contrast between healthy tissue and cauterized tissue or identifies a difference in temperature between the cauterized tissue and the healthy tissue.

In some embodiments, the gastrectomy device 500 may be fabricated from a non-conductive material and may allow for rapid transection of the stomach along the created path. Rapid transection of the stomach is achieved due to the non-conductivity of the gastrectomy device 500, which may protect the surrounding tissue against damage from microwave energy, RF energy, and any other energy that may cause damage to tissue.

Figure 5:
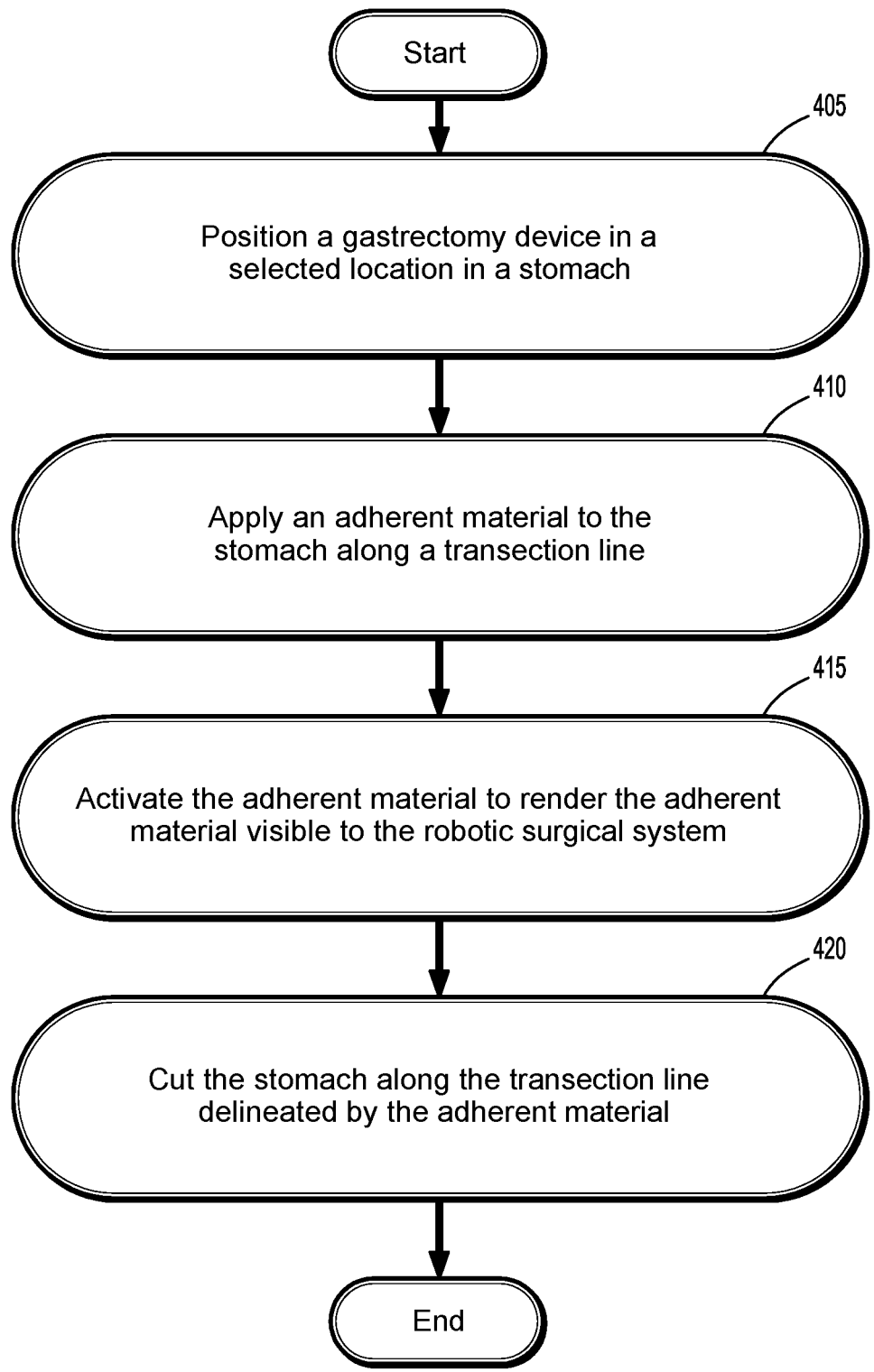
FIG. 5 is a flow chart illustrating an exemplary method of performing bariatric surgery using the robotic surgical system of FIG. 1.

With reference to FIGS. 3-5, an exemplary method for performing a sleeve gastrectomy procedure utilizing the robotic surgical system 1000 will now be described. The gastrectomy device 500 may be inserted into a patient by a clinician or the robotic surgical system 1000. The gastrectomy device 500 is distally advanced toward a stomach of the patient along an enteral pathway that extends from an oral cavity, through an esophagus of the patient, and into the stomach. Lights 570 of gastrectomy device 500 are powered to illuminate sail member 560 and/or gastrectomy device 500 generally. With sail member 560 illuminated, gastrectomy device 500 is guided along the enteral pathway via observation of the illuminated sail member 560. Gastrectomy device 500 is selectively repositioned based on observed positions of the illuminated sail member 560 along the enteral pathway. In embodiments where gastrectomy device 500 is operated by the robot arm 1003, gastrectomy device 500 may be guided through the esophagus using a GPS receiver (not explicitly shown).

In step 405, gastrectomy device 500 is further guided through the esophagus and selectively positioned within the stomach of the patient. Upon positioning gastrectomy device 500 within the stomach, sail member 560 is moved distally through the handle assembly 510 causing sail member 560 to bow outwardly relative to elongated shaft member 540 towards the expanded state, as shown in FIG. 3. As sail member 560 bows outwardly towards the expanded state, elongated shaft member 540 is urged towards and into complementary mating relation with a lesser curvature portion of the stomach, while sail member 560 is urged towards and into complementary mating relation with a greater curvature portion of the stomach. As such, the orientation of gastrectomy device 500 with elongated shaft member 540 extending along the lesser curvature portion of the stomach between the esophageal sphincter and the pyloric sphincter can be readily achieved. As a result of this configuration of gastrectomy device 500 in the expanded state, the above-described orientation of gastrectomy device 500 within the stomach is maintained despite spasms, folding, spiraling, and/or shifting of the stomach.

Once the proper orientation of elongated shaft member 540 has been achieved, suction is applied, by vacuum source "VS," for suctioning any remaining contents within the antrum of the stomach into elongated shaft member 540 through the side apertures 550. Application of suction also suctions the lesser curvature portion of the stomach to an outer surface of elongated shaft member 540 to ensure and maintain the complementary mating relation of elongated shaft member 540 with the lesser curvature portion of the stomach.

With elongated shaft member 540 maintained in position relative to the lesser curvature portion of the stomach as a result of the applied suction, sail member 560 is translated proximally relative to elongated shaft member 540 to return sail member 560 to the first, unexpanded state. As suction is maintained at this point, elongated shaft member 540 is maintained in the position detailed above despite contraction of sail member 560.

Once sail member 560 has been returned to the unexpanded state (i.e., disposed coaxial with longitudinal axis "X"), transection of the stomach adjacent elongated shaft member 540 on an opposite side of elongated shaft member 540 relative to the lesser curvature portion of the stomach may be effected. In particular, in step 410, the clinician, manually controlling the marking device 595, may apply the adherent material 590 to the stomach along a desired transection line "L." In other aspects, instead of a clinician manually applying the adherent material 590 to the delineated transection line "L," the processor of the control unit 1004 (FIG. 1), using the data gathered by the camera, directs the robot arm 1003 to move the surgical instrument along a pathway formed by the lights 570 while dispersing the adherent material 590 onto the stomach.

With the adherent material 590 applied to the stomach along the transection line "L," in step 415, the adherent material 590 may be activated to render the adherent material 590 visible or more visible to the robotic surgical system 1000. For example, the light or heat generated by the lights 570 may activate the adherent material 590 to render it more visible to the sensor of the robotic surgical system 1000 and/or to cure the adherent material 590. In other aspects, a secondary surgical instrument may direct energy, such as, for example, microwave or radiofrequency energy, at the adherent material 590 to activate the adherent material 590. Once the adherent material 590 is visible to the robotic surgical system 1000, in step 420, transections of the stomach may be effected in any suitable fashion along the visible adherent material 590 by the robotic surgical system 1000 or the clincian.

For example, one or more small incisions may be created in the abdomen of the patient for receiving a robotically-controlled instrument therein to perform the transection procedure. Access ports, such as, for example, cannulae (not shown) are inserted into the small incisions made in the abdomen to maintain the small incisions open. In some embodiments, the robotically-controlled surgical instrument, such as, for example, a vessel sealer or surgical stapling instrument is inserted into the patient through the cannula and used to transect the stomach. In aspects, the robotically-controlled surgical instrument may automatically trace the marking device 595 and cut the stomach along the transection line "L" as the marking device 595 marks the stomach.

Transection in this manner reforms the stomach to a tubular-shaped configuration that generally approximates the outer dimension of elongated shaft member 540 and extends between the esophageal sphincter and the pyloric sphincter. As can be appreciated, the diameter of elongated shaft member 540 may be selected in accordance with a desired diameter of the tubular-shape reformed stomach.

In some embodiments, additionally or alternatively, once the stomach is transected, a surgical instrument, such as, for example a vessel sealer may be inserted into the patient through the cannula and additional adherent material 590 may be applied along the transection line. The lights 570 may be activated to activate the adherent material 590, thereby curing the adherent material 590 to seal the tissue along the transection path. As such, the adherent material 590 may serve the dual purpose of rendering the transection line visible to the robotic surgical system 1000 and assisting in sealing the tissue along the transection line.

In some embodiments, the robotic surgical system 1000 may be further configured to measure the dimensions (e.g., length and width) of the desired transection line or the transection line post-cut to assist the clinician in selecting the appropriate staple load that corresponds to the measured dimensions of the transection line.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A method of performing bariatric surgery using a robotic surgical system, comprising:
    positioning a gastrectomy device in a selected location in a stomach;
    manually applying an adherent material to the stomach along a desired transection line;
    emitting light from the gastrectomy device to render the adherent material visible to the robotic surgical system; and
    cutting the stomach along the desired transection line delineated by the adherent material using a robotically-controlled surgical instrument.

2. The method according to claim 1, wherein the adherent material is a surgical glue.

3. The method according to claim 1, further comprising moving a sail member of the gastrectomy device from an unexpanded configuration to an expanded configuration prior to applying the adherent material to the stomach.

4. A method of performing bariatric surgery using a robotic surgical system, comprising:
    positioning a gastrectomy device in a selected location in a stomach;
    expanding a sail member of the gastrectomy device relative to an elongated shaft member of the gastrectomy device to engage a greater curvature of the stomach and urge the elongated shaft member into complementary mating relation with a lesser curvature of the stomach;
    moving a marking device along the stomach to apply an adherent material along a desired transection line subsequent to expanding the sail member; and
    transecting the stomach along the desired transection line delineated by the adherent material using a robotically-controlled surgical instrument.

5. The method according to claim 4, wherein moving the marking device includes applying a physical marking on the stomach.

6. The method according to claim 5, wherein the robotically-controlled surgical instrument automatically transects the stomach along the desired transection line by following the physical marking on the stomach.

7. The method according to claim 4, wherein the adherent material is a surgical glue, and the method further comprises applying heat to the surgical glue, thereby sealing the transection line.

8. The method according to claim 7, wherein the robotically-controlled surgical instrument is an electrosurgical instrument that cuts the stomach along the transection line and applies heat to the stomach along the transection line.

9. The method according to claim 4, wherein the marking device is manually moved by a clinician to define the desired transection line along the stomach.

10. A method of performing a surgical procedure using a robotic surgical system, comprising:
   manually moving a marking device along tissue while applying a surgical glue to the tissue with the marking device along a pathway defined by a plurality of lights of a gastrectomy device, thereby defining a transection line along the tissue;
   applying energy to the surgical glue, thereby enhancing a visibility of the surgical glue to the robotic surgical system; and
   cutting the tissue along the transection line using a robotically-controlled surgical instrument.

11. The method according to claim 10, wherein the robotically-controlled surgical instrument follows behind the marking device and cuts the tissue along the transection line as the marking device moves along the tissue.

12. The method according to claim 10, further comprising applying heat to the tissue along the transection line using the robotically-controlled surgical instrument concurrently with cutting the tissue.

13. The method according to claim 12, wherein the heat applied to the tissue by the robotically-controlled surgical instrument cures the surgical glue to effect a seal of the tissue along the transection line.

14. The method according to claim 10, further comprising:
   positioning the gastrectomy device in a selected location in a stomach prior to moving the marking device;
   expanding a sail member of the gastrectomy device relative to an elongated shaft member of the gastrectomy device to engage a greater curvature of the stomach and urge the elongated shaft member into complementary mating relation with a lesser curvature of the stomach.

15. The method according to claim 14, wherein the plurality of lights are disposed along the sail member.

* * * * *